(12) United States Patent
David et al.

(10) Patent No.: US 9,492,580 B2
(45) Date of Patent: Nov. 15, 2016

(54) SYSTEM AND METHOD FOR THE SAFE PROVISION OF OZONE

(71) Applicants: Eliyahu David, Yodfat (IL); Dror Niv, Atzmon (IL)

(72) Inventors: Eliyahu David, Yodfat (IL); Dror Niv, Atzmon (IL)

( * ) Notice: Subject to any disclaimer, the term of this patent is extended or adjusted under 35 U.S.C. 154(b) by 0 days.

(21) Appl. No.: 14/340,085

(22) Filed: Jul. 24, 2014

(65) Prior Publication Data

US 2016/0022851 A1 Jan. 28, 2016

(51) Int. Cl.
*A61L 2/18* (2006.01)
*A61L 2/20* (2006.01)
*C01B 13/02* (2006.01)

(52) U.S. Cl.
CPC .......... *A61L 2/202* (2013.01); *A61L 2209/212* (2013.01)

(58) Field of Classification Search
CPC ....................................................... A61L 2/202
USPC ......................................................... 422/28
See application file for complete search history.

(56) References Cited

U.S. PATENT DOCUMENTS

| | | | |
|---|---|---|---|
| 3,207,695 A | 9/1965 | Gustafson | |
| 3,736,104 A | 5/1973 | Churchill et al. | |
| 3,861,880 A * | 1/1975 | Thompson | .......... C01B 13/0296 102/530 |
| 4,619,763 A | 10/1986 | O'Brien | |
| 5,578,280 A * | 11/1996 | Kazi | ...................... B01J 19/088 422/186.07 |
| 6,155,254 A * | 12/2000 | Evrard | ................... A62B 21/00 128/202.26 |
| 6,279,589 B1 | 8/2001 | Goodley | |
| 6,585,898 B1 | 7/2003 | Ekberg et al. | |
| 7,137,621 B1 | 11/2006 | Bagley | |
| 2002/0027109 A1* | 3/2002 | Conrad | ................... A61L 2/202 210/760 |
| 2005/0236338 A1 | 10/2005 | Minnix | |
| 2007/0251549 A1* | 11/2007 | Heiligenmann | .... A47L 15/0015 134/31 |
| 2008/0241052 A1 | 10/2008 | Hooper et al. | |
| 2009/0233839 A1* | 9/2009 | Lynn | ....................... A61L 2/183 510/370 |
| 2011/0030730 A1 | 2/2011 | Lynn | |
| 2011/0271479 A1* | 11/2011 | Bertram | .................... A47L 9/19 15/339 |

FOREIGN PATENT DOCUMENTS

| | | |
|---|---|---|
| EP | 1335680 A1 | 8/2003 |
| EP | 2662008 A1 | 11/2013 |
| WO | 2013007979 A1 | 1/2013 |

* cited by examiner

*Primary Examiner* — Kevin Joyner
*Assistant Examiner* — Holly Mull
(74) *Attorney, Agent, or Firm* — Browdy and Neimark, PLLC

(57) ABSTRACT

A household appliance system for safe generation and delivering of ozone comprising at least one disposable capsule, each capsule is configured to chemically generate a predetermined dose of oxygen wherein the disposable capsule is manipulated in a way that initiates generation of oxygen, and an ozone generator for generating ozone from said predetermined dose of oxygen, wherein the ozone generator is fluidically connected to said capsule.

18 Claims, 8 Drawing Sheets

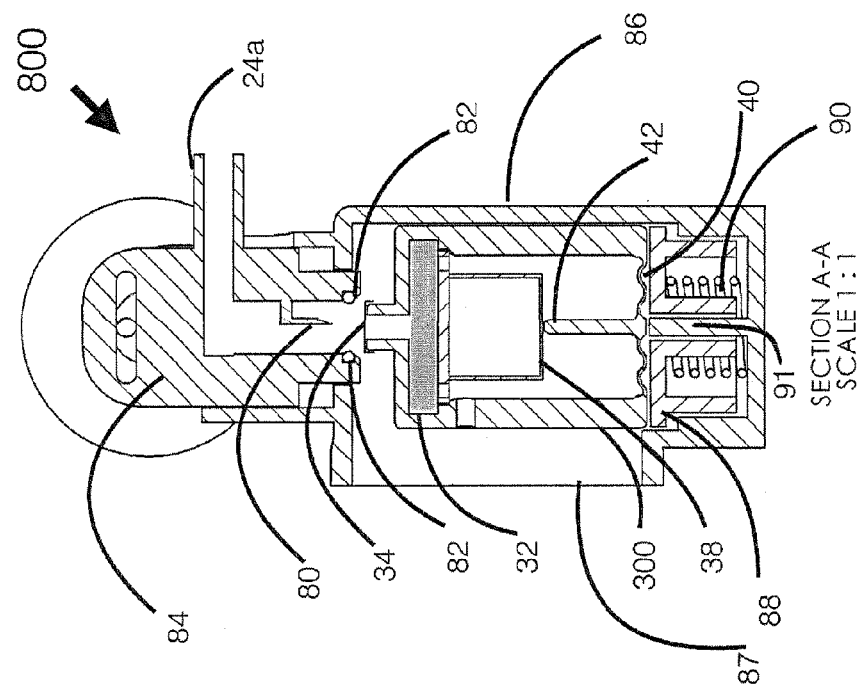
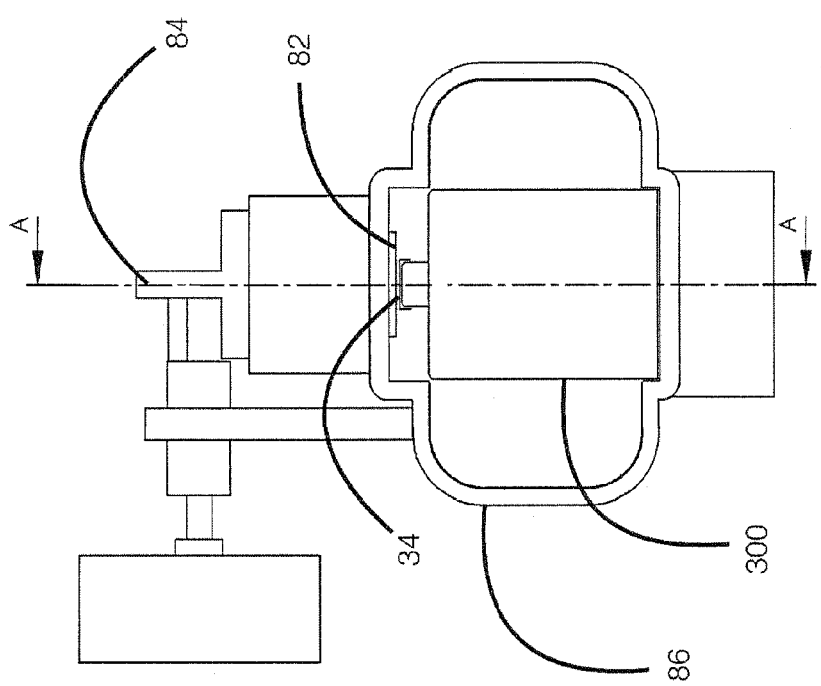
Fig. 3b
Fig. 3a

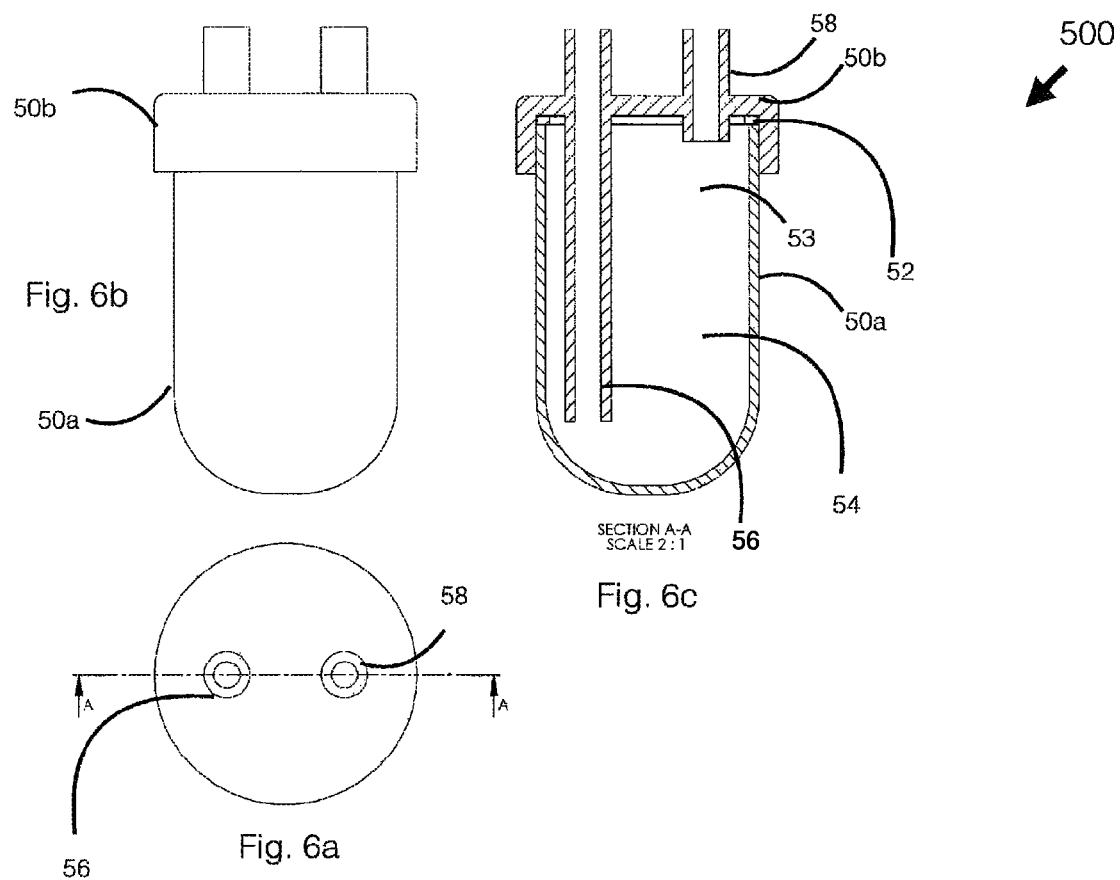

SYSTEM AND METHOD FOR THE SAFE PROVISION OF OZONE

FIELD OF THE INVENTION

The present invention relates generally to the field of ozone generators and more specifically to on-demand generation of ozone and ozone-rich liquids that may be utilized effectively and safely in a wide array of applications from personal hygiene to surface sanitation.

BACKGROUND OF THE INVENTION

Liquids 'impregnated' with ozone otherwise known as 'ozonated liquids' or 'ozone-rich solutions', provided that a proper concentration and dispersion of the ozone within the liquid is achieved, are useful for the sanitation of surfaces, as an antiseptic, for the topological treatment of skin conditions and wounds, for maintaining general well-being, and for expediting the healing process of infections in both dental and medical applications. However, health and safety concerns in the medical and dental application of ozone, be it gaseous or liquid-impregnated, entail that it must be free of contaminants or by-products, and therefore must be produced from pure oxygen.

This has traditionally been achieved, for example in HealOzone™ commercial products, by utilizing a medical grade oxygen canister that is free from the impurities found in ambient air, or alternatively by generating oxygen locally by means of an electrical apparatus for separating the impurities and the moisture found in ambient air from the pure oxygen it contains. Both these traditional approaches have shortcomings, the former requires the transportation, storage and handling of oxygen canisters that may present a safety hazard if proper pressure, heat, and spark conditions cannot be strictly controlled (for example in a typical residential household), and indeed oxygen canisters have been barred on commercial airlines; the latter requires a bulky and noisy air-pump based component, thereby consuming energy, restricting the possibility of both the miniaturisation of the device and its placement (again for example in a typical residential household), and generating production as well as maintenance costs related to the mechanical components that are employed.

Moreover, even if medical grade ozone output is not required (for example for surface sanitation), once a source of pure oxygen is not employed, in order to generate substantial ozone at a reasonable rate (i.e. gram per hour) one would require the use of a cumbersome conventional electrical air 'dryer' for the purpose of dehumidification, as disclosed in US patent application 2005/236338 (MINNIX): 'Meanwhile, oxygen (O2) enters dryer 57 where it is dried in preparation for conversion to ozone (O3). The dried oxygen (O2) flows to ozone generator 56, which produces ozone (O3) from the dried oxygen (O2).', or similarly in the system for water purification of U.S. Pat. No. 4,619,763 (O'BRIEN) as disclosed in claim 1 therein ' . . . (c) means for chilling and thereafter drying the ambient air prior to its being passed through said ozone generator;'.

The direct application of gaseous ozone for medical or dental purposes, for example as disclosed in European patent 1335680 (CUROZONE), presents environmental challenges with respect to preventing the exposure of unintended tissue and organs to ozone gas, as well as the environmental damage associated with the uncontrolled release of ozone to the general environment. Hence CUROZONE teaches: 'A cup attached to the hand piece, is provided for receiving the gas and exposing a selected area of the tooth to the gas. The cup may include a resilient edge for sealably engaging the tooth around the selected area to prevent escape of the gas therepast.', and 'In that regard a controller may be provided for regulating the ozone and aspiration pumps in order to circulate the gas into and out of the cup chamber at a pressure insufficient to escape past the sealed engagement between and the tooth.' However, these measures for preventing ozone leakage rely on professionally applied sealants and high maintenance aspiration pumps that are suited both technologically (noise, physical volume, maintenance, ease-of-use) and ultimately also economically for a professional environment (e.g. a dental practice), rather than for use by a layperson in a residential environment.

Ozone can also be used in sanitary, medical, and dental applications by impregnating a liquid with ozone. Ozonated liquid mostly captures the ozone within it, and is not easily aspirated (gaseous ozone can cause irritation and damage to the respiratory system) therefore its application presents a highly reduced 'health and safety' risk, and makes it suitable for use in home appliances, provided that any ozone off-gas, produced during the impregnating process or the temporary storage of the impregnated liquid, is contained or safely decomposed.

To assure the balance between the effectiveness in the application of an ozonated liquid on the one hand, and the safety of the application on the other, one must control the concentration of ozone within the dispensed ozonated liquid. GB patent application 2012/051502 (HESKETH) discloses 'a device for supply of ozonated liquid, comprising a liquid reservoir, a supply passage which communicates with the reservoir and is connectable to an outlet of an ozone generator and a pump for circulating fluid in a loop in which the fluid passes from the reservoir to the ozone generator back to the reservoir through the passage . . . ', in which 'By circulating the water in this closed loop for a period of time, the ozone concentration in the reservoir 16 is progressively increased and relatively high concentrations can be achieved.' Moreover, HESKETH further discloses that 'Some means of control is required to ensure that an adequate concentration of ozone is achieved.', and goes on to offer that 'This may simply be achieved by a timer which causes the pump 36 and the ozone generator to run for a chosen period.' or alternatively 'to actively monitor ozone concentration, which may be achieved through a sensor (not shown) mounted e.g. in the reservoir 16.' Similarly MINNIX teaches 'The amount of ozone generated may be adjusted according to the amount of ozone sensed in the water.'; and likewise in the Method and apparatus for preparation and use of ozone water of U.S. Pat. No. 6,585,898 (OTRE AB) claim 1 teaches: ' . . . ozone measuring means (51) for measuring the ozone concentration of said water in the container (60).'

Furthermore HESKETH teaches that due to the 'relatively expensive ozone generator' component, in order not to hinder mobility and cost-effectiveness, once the 'Fluid 18 (typically water) is circulated through the ozone generator as so charged with ozone . . . the unit 10 can be disconnected from the ozone generator and taken to a point of use (e.g. hospital ward).', thereby allowing the use of a plurality of ozonated liquid delivery units with a single ozone generator. Indeed HESKETH cites the lack of an onboard ozone generator as a cost-effective technological advantage when compared with the cleaning and disinfecting apparatus disclosed in U.S. Pat. No. 6,279,589 (GOODLEY). Still both HESKETH and GOODLEY rely on the time-consuming circulation of the liquid in order to increase the ozone concentration, as taught by GOODLEY: 'a recirculating system for recirculating the combined water and ozone from the holding tank through the venturi for increasing the ozone concentration'. Likewise, MINNIX teaches recirculation as a means for achieving increased ozone concentration, or otherwise referred to as 'super-impregnation': 'The ozone is then passed to venturi 34, which injects the unsterilized water with the ozone to produce ozonated (sterile) water. The ozonated water then flows from venturi 34 to holding tank 38 via pipe 52. The ozonated water is drawn from holding tank 28 back to pump 24 via pipe 54, and is either recirculated to venturi 34 for super-impregnation of ozone, or released to tap 32.'.

It is therefore a long-felt need to provide a system and method for the provision of the medical and dental benefits availed by exposure to medical-grade ozone, that overcomes the safety issues relating to transport, storage and handling, associated with the conventional use of 'onboard' pressurised pure-oxygen as the source gas for medical-grade ozone. It is a further long-felt need to provide a system and method for the medical and dental benefits availed by exposure to medical-grade ozone, that overcomes the cumbersome volume, noise, maintenance, and cost associated with the conventional use of an onboard oxygen generator or air separator as the provider of a source gas for medical-grade oxygen. It yet another long-felt need to provide a system and method for the provision of the hygiene and sanitation effects availed by the exposure of areas and surfaces to an effective amount or concentration of ozone, without the cumbersome bulk, the noise, the cost, the maintenance, associated with the conventional use an air dryer or air cooler. It is yet another long-felt need to provide a system and method for the provision of the medical, dental, hygiene and sanitation effects availed by the controlled exposure of areas and surfaces to ozone, without the cumbersome bulk, the noise, the cost, the maintenance, the professional infrastructure, and professional operation, in conventional gaseous ozone delivery systems. It is yet another long-felt need to provide a system and method for the provision of the medical, dental, hygiene and sanitation effects availed by the controlled exposure of areas and surfaces to an ozone-rich solution, which overcomes the time-consuming, cumbersome, maintenance-heavy and costly utilization of repeated circulation of the liquid through means for impregnating the liquid with ozone, or otherwise repeatedly impregnating the liquid with ozone, in order to achieve an adequate concentration of ozone within the liquid. It is a further long-felt need to provide a system and method for the provision of the medical, dental, hygiene and sanitation effects availed by the controlled exposure of areas and surfaces to an ozone-rich solution at a particular concentration adequate for a particular application, that overcomes reliability, placement and maintenance difficulties brought on by the conventional usage of a sensor placed in contact with the liquid. It is a further long-felt need to provide a system and method for the provision of the medical, dental, hygiene and sanitation effects availed by the controlled exposure of areas and surfaces to an ozone-rich solution at a particular concentration adequate for a particular application, that overcomes the perplexity often brought on in a layperson when confronted with the manual setting of a particular concentration by conventional control panel means, and the risk of accidentally operating the system at an unintentional setting and consequently delivering an ozone-rich solution at an undesired or even harmful concentration. It is yet another long-felt need to provide a system and method for the provision of the sanitation, hygiene, dental and medical benefits of gaseous ozone or an ozone-rich solution in a device of non-bulky unobtrusive dimensions, that avoids the complexity in operation and maintenance-heavy, cost, and safety issues that have typically restricted the provision of devices that are capable of safely delivering effective ozone amount or concentration to non-professional users in non-professional settings.

SUMMARY OF THE INVENTION

Methods, systems, and other means are provided for a device that safely generates ozone and ozone-rich solution in a household environment.

It is an object of the present invention to provide a household appliance system for safe generation and delivering of ozone comprising: at least one disposable capsule, each capsule is configured to chemically generate a predetermined dose of oxygen wherein the disposable capsule is manipulated in a way that initiates generation of oxygen; an ozone generator for generating ozone from the predetermined dose of oxygen, wherein the ozone generator is fluidically connected to the capsule.

It is a further object of the present invention to provide a household appliance system, wherein a plurality of disposable capsules with different predetermined doses of oxygen are available so that a user can select an appropriate disposable capsule so as to generate an amount of ozone that is needed.

It is a further object of the present invention to provide a household appliance system, wherein the ozone generator is powered as long as oxygen flow to said ozone generator is maintained.

It is a further object of the present invention to provide a household appliance system, further comprising a user interface through which chemical generation of oxygen is initiated.

It is a further object of the present invention to provide a household appliance system, further comprising a sensor positioned between the disposable capsule and the ozone generator, wherein the sensor is configured to sense the flow of oxygen so that accordingly, power to the ozone generator is regulated.

It is a further object of the present invention to provide a household appliance system, wherein to disposable capsule is received within a receptacle that is configured to manipulate the capsule so as to allow flow of oxygen from the capsule to t ozone generator.

It is a further object of the present invention to provide a household appliance system, wherein said ozone generator is selected from a group of ozone generators comprising: corona discharge electrode, cold plasma, UV light, vacuum UV light, or a combination thereof.

It is a further object of the present invention to provide a household appliance system, further comprising a container for receiving a liquid into which ozone from the ozone generator is dissolved and diffused so as to produce ozone-rich solution.

It is a further object of the present invention to provide a household appliance system, wherein the liquid is of a predetermined volume so as to control the ozone concentration within the ozone-rich solution.

It is a further object of the present invention to provide a household appliance system, wherein the ozone-rich solution is dispensed through a liquid jet.

It is a further object of the present invention to provide a household appliance system, wherein excess gaseous ozone from the container is decomposed in a filter from which resultant oxygen is dispensed to the environment.

It is a further object of the present invention to provide a household appliance system, wherein at least one level sensor is provided to the container so as to maintain a desirable level range of liquid.

It is a further object of the present invention to provide a household appliance system, wherein the ozone generator is a corona discharge ozone generator that is configured with a sterile electrode and wherein the ozone is of medical grade.

It is a further object of the present invention to provide a household appliance system, wherein the at least one disposable capsule is recyclable.

It is yet another object of the present invention to provide a household appliance system, wherein the disposable capsule comprising: at least two compartments, each of the compartments is provided with a chemical component; at least one impermeable barrier separating the at least two compartments one from the other wherein disruption of the impermeable barrier allows the chemical components to react and to generate oxygen; a lance for disrupting the impermeable barrier: and at least one opening for releasing generated oxygen from the disposable capsule.

It is a further object of the present invention to provide a household appliance system, further comprising filter between the disposable capsule and the ozone generator.

It is a further object of the present invention to provide a household appliance system, wherein the filter is selected from a group of filters comprising: selective membrane, gas washer, or a combination thereof.

It is a further object of the present invention to provide a household appliance system, further comprising monitoring indicator for indicating saturation of the filter, wherein the monitoring indicator is selected from a group of indicators comprising: see-through window for direct view of the filter, audio or visual indicator fluidically connected to a sensor, or a combination thereof It is a further object of the present invention to provide a household appliance system, wherein the household appliance system is for applications selected from a group of applications comprising sanitation, hygiene, dental, medical, or a combination thereof.

It is yet another object of the present invention to provide a disposable capsule for chemically generating a predetermined dose of oxygen to be used in an ozone generator comprising: at least two compartments, each of the compartments is provided with a chemical component; at least one impermeable barrier separating said at least two compartments one from the other, wherein disruption of said impermeable barrier allows the chemical components to react and to generate oxygen; a sealed opening to allow collection of oxygen; and a lance for disrupting said impermeable barrier.

It is a further object of the present invention to provide a disposable capsule for chemically generating a predetermined dose of oxygen to be used in an ozone generator, wherein said lance is fluidically connected to one end of said capsule, and said one end is configured to conduct external manipulation of said capsule through said lance to said impermeable barrier.

It is a further object of the present invention to provide a disposable capsule for chemically generating a predetermined dose of oxygen to be used in an ozone generator, further comprising an gas selective at the sealed opening.

It is a further object of the present invention to provide a disposable capsule for chemically generating a predetermined dose of oxygen to be used in an ozone generator, wherein the disposable capsule is marked so as to indicate the predetermined dose of oxygen.

It is a further object of the present invention to provide a disposable capsule for chemically generating a predetermined dose of oxygen to be used in an ozone generator, wherein the disposable capsule is provided with a pressure release valve as safety means.

It is yet another object of the present invention to provide a method for on-site safe generation and delivering ozone at a specific amount comprising: providing an oxygen-based ozone generator; loading a disposable capsule, wherein said disposable capsule is configured to chemically generate a predetermined dose of oxygen; initiating generation of a predetermined dose of oxygen; allowing said predetermined dose of oxygen from the capsule to flow through said oxygen-based ozone generator so that ozone is generated and can be delivered.

It is a further object of the present invention to provide a method for on-site safe generation and delivering ozone at a specific amount, wherein said disposable capsule comprises: at least two compartments, each of the compartments is provided with a chemical component; at least one impermeable barrier separating said at least two compartments one from the other, wherein disruption of the impermeable barrier allows the chemical components to react and to generate oxygen; a sealed opening to allow collection of the predetermined dose of oxygen; and a lance for disrupting said impermeable barrier; wherein the method further comprising manipulating said the opening to allow flow of oxygen.

It is a further object of the present invention to provide a method for on-site safe generation and delivering ozone at a specific amount, further comprising passing the ozone through a diffuser into a liquid so as to produce ozone-rich solution.

It is a further object of the present invention to provide a method for on-site safe generation and delivering ozone at a specific amount, further comprising dispensing the ozone-rich solution through a liquid jet.

It is a further object of the present invention to provide a method for on-site safe generation and delivering ozone at a specific amount, further comprising decomposing ozone that is not dissolved or impregnated in the solution.

It is a further object of the present invention to provide a method for on-site safe generation and delivering ozone at a specific amount, further comprising monitoring flow of oxygen by a flow sensor.

BRIEF DESCRIPTION OF THE INVENTION

In order to better understand the invention and its implementation in practice, a plurality of embodiments will now be described, by way of non-limiting example only, with reference to the accompanying drawings, in which FIG. 1 illustrates a schematic operational view of a preferred embodiment of the household appliance system for safe generation and delivering of ozone.

FIG. 2a illustrates a side view of a preferred embodiment of the disposable capsule.

FIG. 2b illustrates a cross-section view of a preferred embodiment of the disposable capsule, shown in FIG. 2a.

FIG. 3a illustrates a side view of a preferred embodiment of capsule receptacle mechanism.

FIG. 3b illustrates a cross-section view of a preferred embodiment of capsule receptacle mechanism shown in FIG. 3a.

FIG. 6a illustrates top view of a preferred embodiment of a filter, wherein the filter is a gas-washer.

FIG. 6b illustrates side view of the filter shown in FIG. 6a.

FIG. 6c illustrates cross-section view of the filter shown in FIG. 6a.

Figure 8:
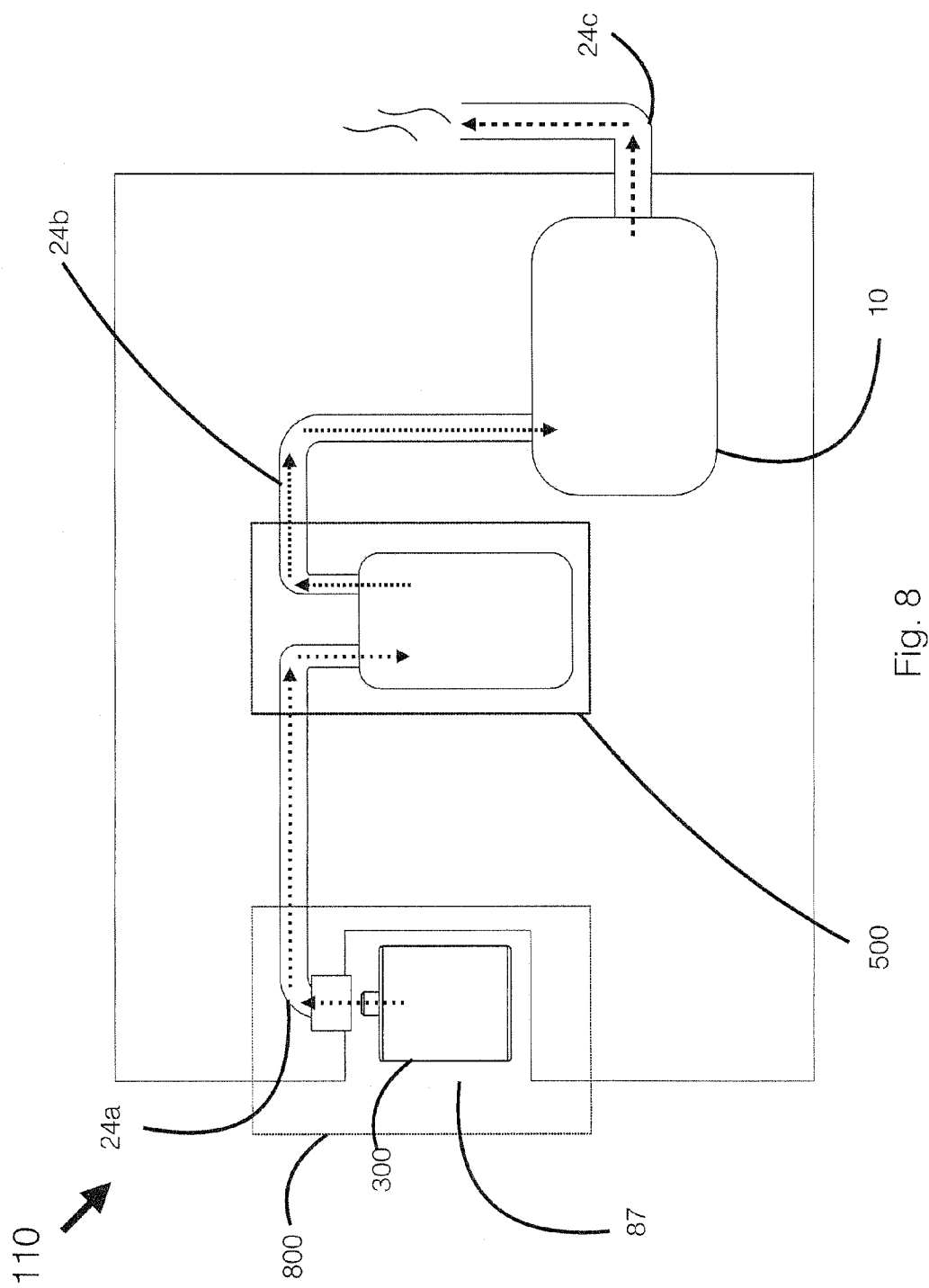

FIG. 8 illustrating a schematic operational view of yet another preferred embodiment of the household appliance system for safe generation and delivering of ozone.

DETAILED DESCRIPTION OF THE INVENTION

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a household appliance system for safe generation and delivering of ozone.

The device and method of the present invention has many technological advantages, among them:
enabling reduced physical dimensions;
enabling hazard-free storage, transport and placement;
enabling risk-free operation by a layperson;
reducing noise-pollution;
lowering energy consumption;
reducing components, and thereby production and maintenance costs;
providing ease-of-use; and,
simplifying the achievement of a an application-tailored amount or concentration of ozone within an ozonated liquid.

Additional features and advantages of the invention will become apparent from the following drawings and description.

The term 'ozone generator' refers hereinafter to any means for generating ozone utilizing a selected a technology selected from a group including: corona discharge, cold plasma, UV light, vacuum UV light, or a combination thereof.

The term 'corona discharge ozone generator' refers hereinafter to a technology that utilizes electrical discharge in order to convert oxygen into ozone.

The term 'electrode' refers hereinafter to a means for producing electrical discharge.

The term 'sterile electrode' refers hereinafter to an electrode that is engulfed in material that is resistant to oxygen and ozone (for example glass), and does not corrode due to exposure to ozone or sensitive to the corona and does not produce by-products other than ozone in the reaction that occurs by exposing oxygen to an electrical discharge.

The term 'household appliance' refers hereinafter to an electrical appliance of moderate dimensions that is suitable for safe storage, placement and usage within the home, by a non-professional user. Notwithstanding the suitability of the 'household appliance' for home operation by a non-professional user, the term should not be construed to limit the reconfiguration of the appliance by those skilled in the art to either outdoor or professional settings.

The terms 'safe' or 'safety' refer hereinafter interchangeably to various aspects of health and safety issues relating to the integrity of a device, its operation, its maintenance, the product it produces and ultimately the risk that any of the above might present to its user or operator, selected from a list including: placement, handling, environmental conditions, storage, usage, active damage prevention, passive damage prevention, or a combination thereof.

The terms 'ozonated liquid', 'ozone impregnated liquid' and 'ozone-rich solution' refer hereinafter interchangeably to a liquid, typically water, that is impregnated with ozone by diffusing gaseous ozone to the liquid. The resulted liquid contains soluble ozone and ozone bubbles.

The term 'medical grade' refers hereinafter to at least one of a set of geopolitically-contingent medical or dental standards that designate a substance is approved for a form of application selected from a group consisting of: open wound application, topological application, injection, inhalation, ingestion, surface sanitation, or a combination thereof.

The term 'medical grade ozone' refers hereinafter to gaseous ozone that is free of contaminants or by-products produce during the ozone generation process.

The term 'excess ozone' refers hereinafter to a by-product of the process of impregnating a liquid with ozone or the temporary storage of ozone-rich liquid, and must therefore be contained and decomposed to prevent it leaking into the environment.

The term 'ozone filter' refers to a means for decomposing ozone-off gas into benign oxygen.

The term 'computer processor' refers hereinafter to a computer processing means that is capable of receiving data from sensor and electronically controlling the electrical operation of a device or system, or parts thereof.

The term 'user interface' refers hereinafter to means for monitoring and controlling a device, system, or parts thereof.

The term 'visual indication' refers hereinafter to an indication availed to the user by visual means selected from a group consisting of: a see-through window, a light, a bulb, a signal, a written message, or a combination thereof.

The term 'liquid level sensor' refers hereinafter to a means for determining the volume of liquid within the container.

The term 'gas washer' refers hereinafter to a means for a filtering a gas by bring it in contact with or seeping it through a liquid.

The term 'substantially moderate physical dimensions' refers hereafter to the weight and volume of a device comparable to the typical size of a countertop small home appliance such as a standard mixer or food processor.

The term 'household' or 'household environment' refers hereinafter to the uncontrolled and varying environmental conditions such as humidity, temperature, pressure, dust, sparks, open-fire, etc., as opposed to the controlled environment that may be achieved in a professional setting such as a hospital, a clinic, a purpose built sanitation facility, etc.

Figure 1:
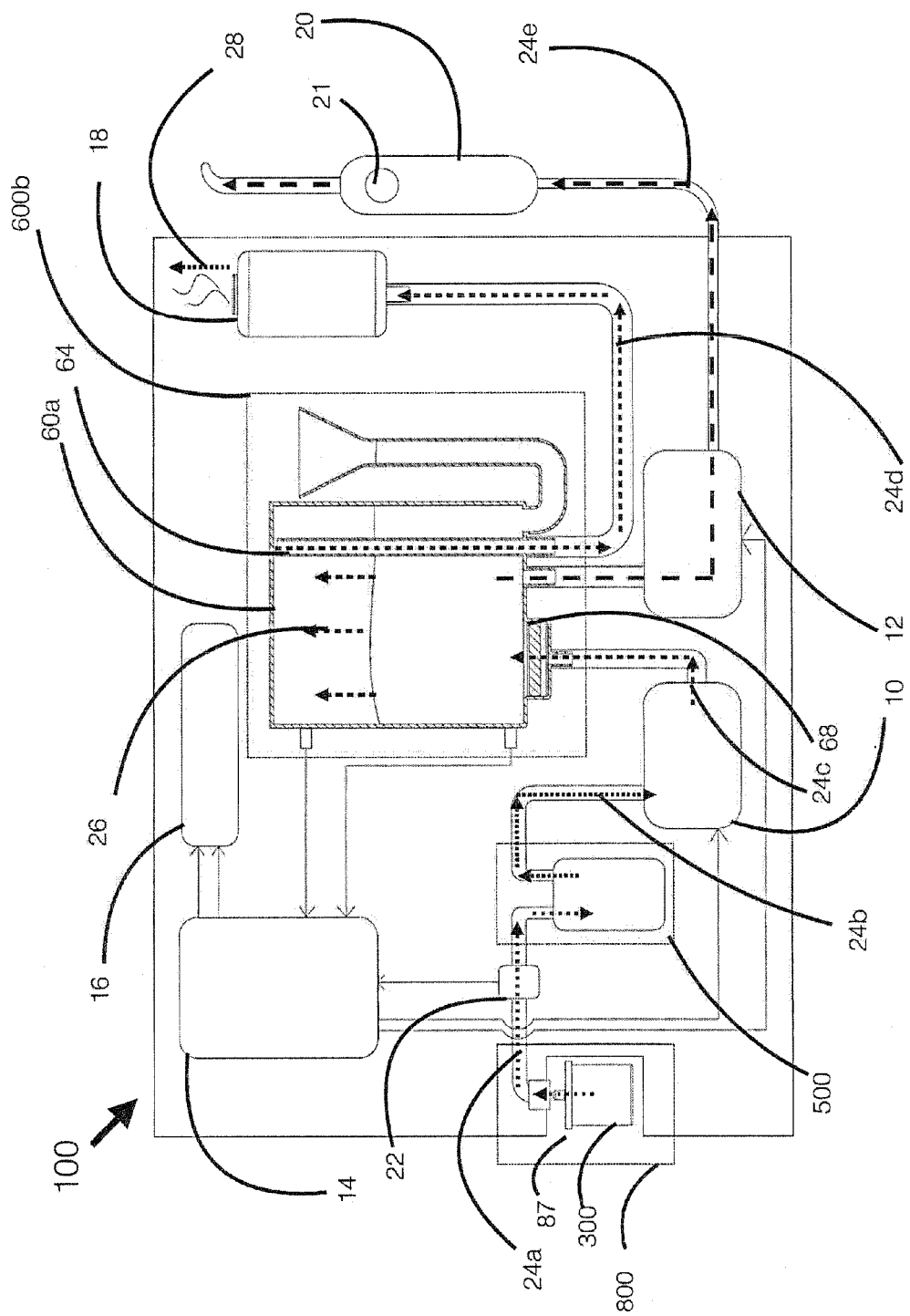

Reference is now made to FIG. 1, illustrating a schematic operational view of a preferred embodiment (100) of the household appliance system for safe generation and delivering of ozone of the present invention, wherein a disposable capsule (300) encapsulating at least two separated components (not shown) of a chemical reaction based generation of a predetermined dose of oxygen, is placed through opening (87) in receptacle mechanism (800) and thereby sealably connected to oxygen delivery tube (24a). Upon instruction by the user by means of user interface (16) and mediated by computer processor (14) the separation between the chemical components is mechanically disrupted (not shown) and oxygen generated by the reaction flows through oxygen flow sensor (22) and subsequently through gas-wash oxygen filter (500) to be delivered by filtered-oxygen delivery tube (24*b*) to ozone generator (10), wherein data from the flow sensor mediated by the computer processor, triggers the application of voltage to the ozone generator for the duration of detected oxygen flow; thereby generating a predetermined amount of ozone that matches the dose of oxygen flowing through the ozone generator during the duration of voltage application. The ozone farther flowing by ozone delivery tube (24*c*) to ozone impregnation system (600*b*) and impregnating liquid contained in container (60*a*) with the ozone by means of ozone gas impregnator (68); further instruction by conventional button interface (21) embedded in ozone-rich delivery jet (20) and mediated by the computer processor triggers the operation of liquid pump (12) that pumps the ozone-rich liquid contained within the container through ozone-rich liquid delivery tube (24*e*) to the delivery jet; further excess ozone (26), by-product of the liquid impregnation, is funneled by excess ozone exhaust (24*d*) through ozone decomposition filter (18) thereby decomposing the excess ozone into oxygen flow (28) that is safely released into the environment.

Figures 2A, 2B:
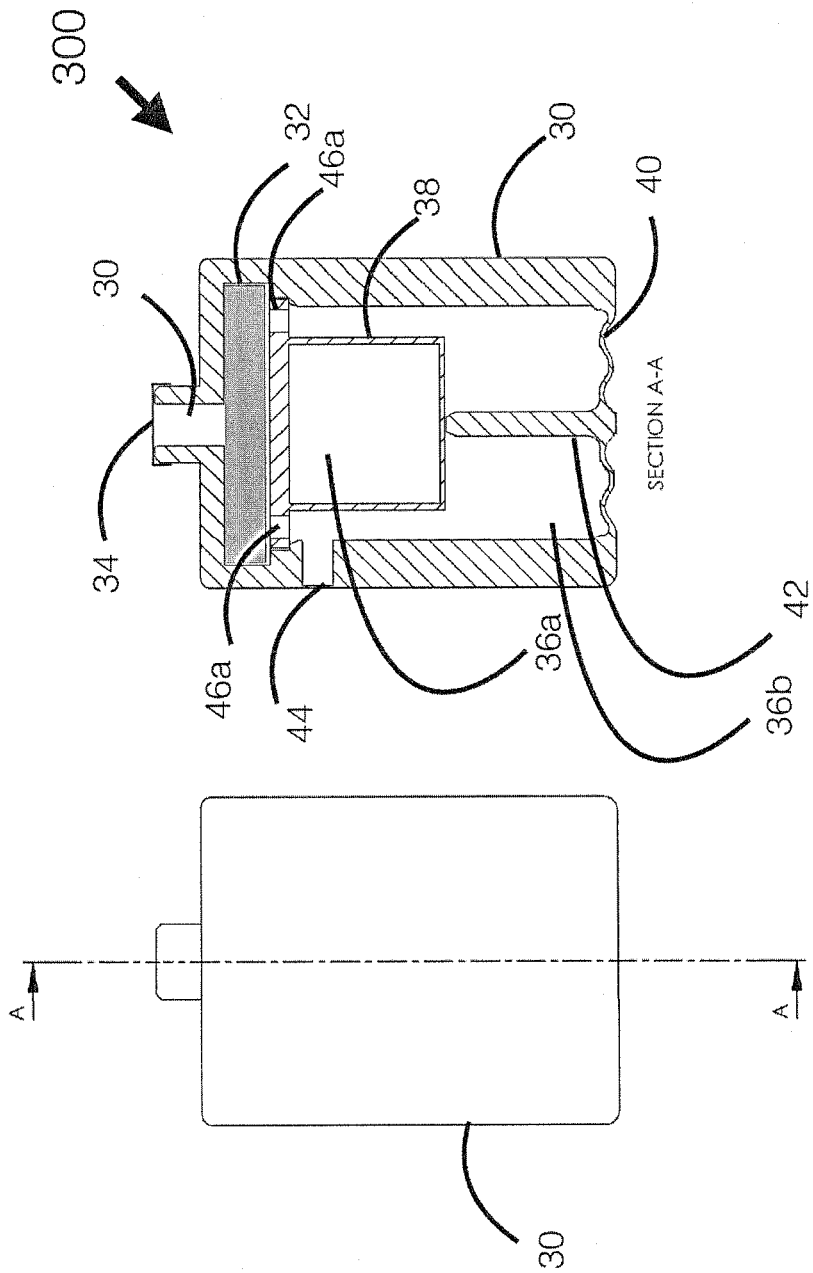

Reference is now made to FIG. 2*a*, FIG. 2*b*, respectively illustrating a side and cross-section view of a preferred embodiment of the disposable capsule (300) of the present invention, wherein a first chemical reaction component, preferably a water based solution of MnO2, is contained within a first compartment (36*a*) and is separated by means of impermeable barrier (38) from a second chemical component that is contained within a second compartment (36*b*) and the two compartments are encapsulated by essentially cylindrical capsule housing (30) having one end (40) adapted to be corrugated and incorporating an integral lance (42) protruding inwardly though the second chemical component and ending in tangent with the corresponding end of the impermeable barrier; the opposite end of the one end of the capsule is configured with outwardly protruding opening (30) sealed at one end by seal (34) configured to prevent moisture from entering the capsule during storage and at its opposite end is in fluid communication with gas selective membrane (32) that is in fluid communication with the second compartment by means of openings (46*a*). The membrane can be an oxygen selective membrane. When the barrier is disrupted, the two components mix and react to generate gaseous oxygen that pass through the opening of the capsule. The capsule is further provided with pressure release safety-valve (44), preferably a weak-point in the capsule housing, configured to release pressure build-up within the capsule in the event of an obstruction in the intended oxygen flow path provided by the openings (46*a*) and (30).

Reference is now made to FIG. 3*a*, 3*b*, respectively illustrating a side and cross-section view of a preferred embodiment (800) of the capsule receptacle mechanism of the present invention. Capsule (300) is loaded through opening (87) into receptacle housing (86) that comprises at one end a connector fluidically capable of connecting the capsule with the oxygen delivery tube 24*a*. The connector is provided with a rupturing means such as a needle (80) that is pointing towards the seal (34). At the opposite end of the capsule, the capsule is provided with a corrugated end (40) and the lance (42), beneath which a platform (88) is provided that is capable of mechanically moving against a spring (90). A fixed pin (91) is preferably provided within the spring 90 so that when the capsule is moving towards the platform, forcing it to move downwardly, the pin is pushing the lance (42) due to the corrugated end (40) so as to enable it to rupture the impermeable barrier (38) and allow the chemicals to mix. Upon movement of the connector (84) downwardly, the opening (30) and the tube (24*a*) are seleangly connected by an o-ring (82) and needle 80 is rupturing the seal (34). As explained, the capsule is moving towards the platform while the lance is rupturing the impermeable barrier and the reaction to generate oxygen takes place. The oxygen then can escape through opening (30) to the oxygen delivery tube through the ruptured seal. The oxygen passes through the gas selective membrane.

Figure 4:
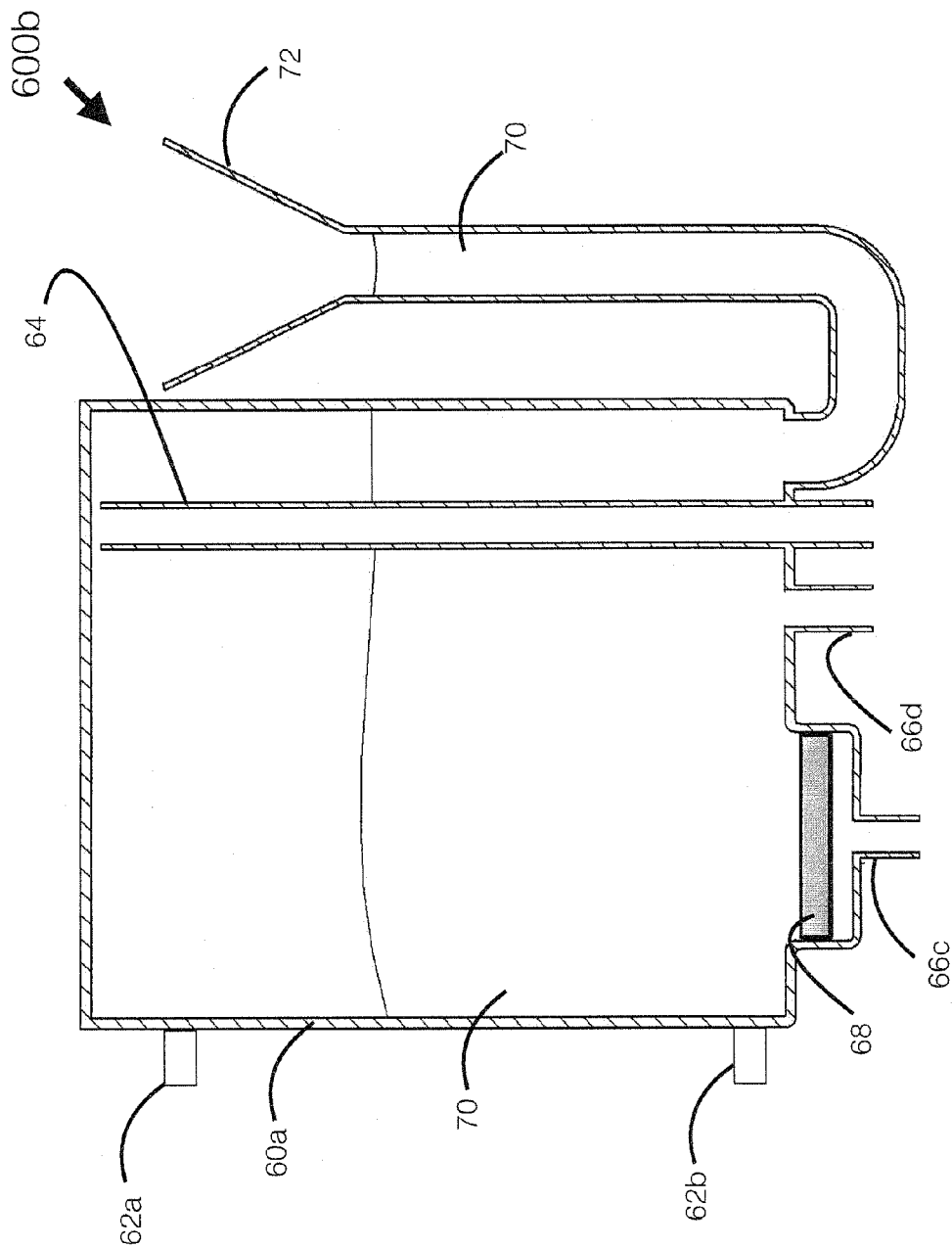
FIG. 4 illustrates a cross-section view of a preferred embodiment of ozone impregnation system.

Reference is now made to FIG. 4 illustrating a cross-section view of a preferred embodiment (600*b*) of the ozone impregnation system of the present invention, wherein liquid (70) is filled by pouring liquid into funnel opening (72), wherein the funnel opening is a lower position than an ozone exhaust 64 so as to assure the exhaust stays open; the container is further configured with ozone inlet opening (66*c*) in fluid communication with diffuser (68) for impregnating the liquid with ozone, and ozone-rich liquid outlet opening (66*d*); the container is further adapted with minimum liquid level sensor (62*b*) and excess liquid level sensor (62*a*), preferably mounted on the outer side of container (60*a*), the container is further configured with excess ozone exhaust (64).

Figures 5A, 5B:
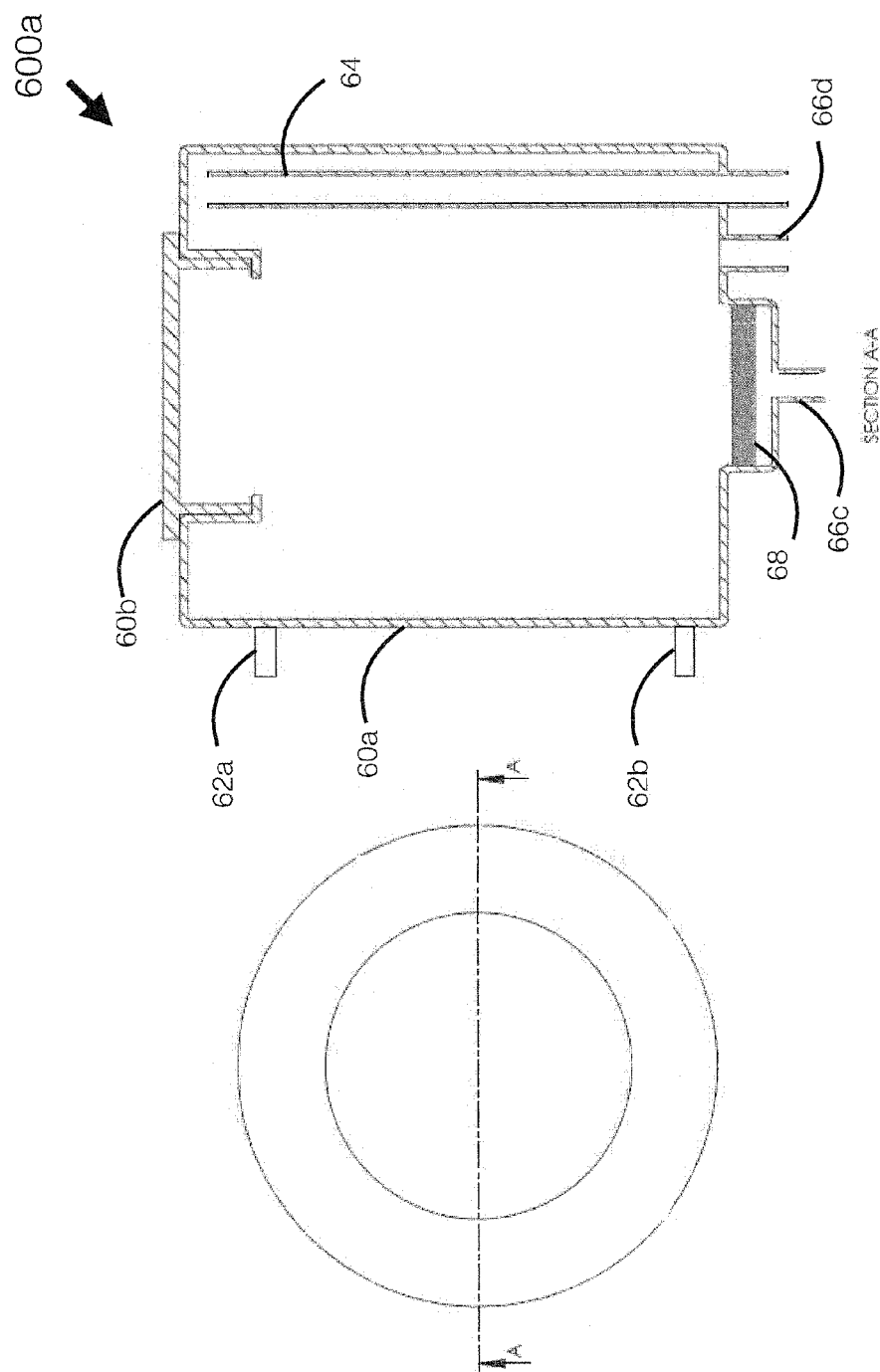
FIG. 5a illustrates a top view of yet another preferred embodiment of ozone impregnation system.
FIG. 5b illustrates a cross-section view of yet another preferred embodiment of ozone impregnation system.

Reference is now made to FIG. 5*a*, 5*b* respectively illustrating a top and cross-section view of another preferred embodiment (600*a*) of the ozone impregnation system of the present invention, comprising container (60*a*) sealed by container lid (60*b*), wherein the container is further adapted with ozone inlet opening (66*c*) in fluid communication with impregnator (68) for impregnating the liquid with ozone, and ozone-rich liquid outlet opening (66*d*); the container is further configured with minimum liquid level sensor (62*b*) and excess liquid level sensor (62*a*), preferably mounted on the outer side of the container, the container is further configured with excess ozone exhaust (64).

Reference is now made to FIG. 6*a*, 6*b*, 6*c* respectively illustrating top, side and cross-section views of a preferred embodiment (500) of the oxygen filter of the present invention, wherein the filter is a gas-washer, comprising: liquid container (50*a*) containing liquid (54), and matching o-ring (52) sealable lid (50*b*), wherein the lid is configured with inlet tube (56) that protrudes inwardly into the container such that it extends beyond the upper level of the liquid, and with an outlet tube (58) that protrudes inwardly into the container such that it extends into gas-gap (53); such that oxygen entering through the inlet is washed in the liquid, bubbles into the gas-gap and exits through the outlet.

Figure 7:
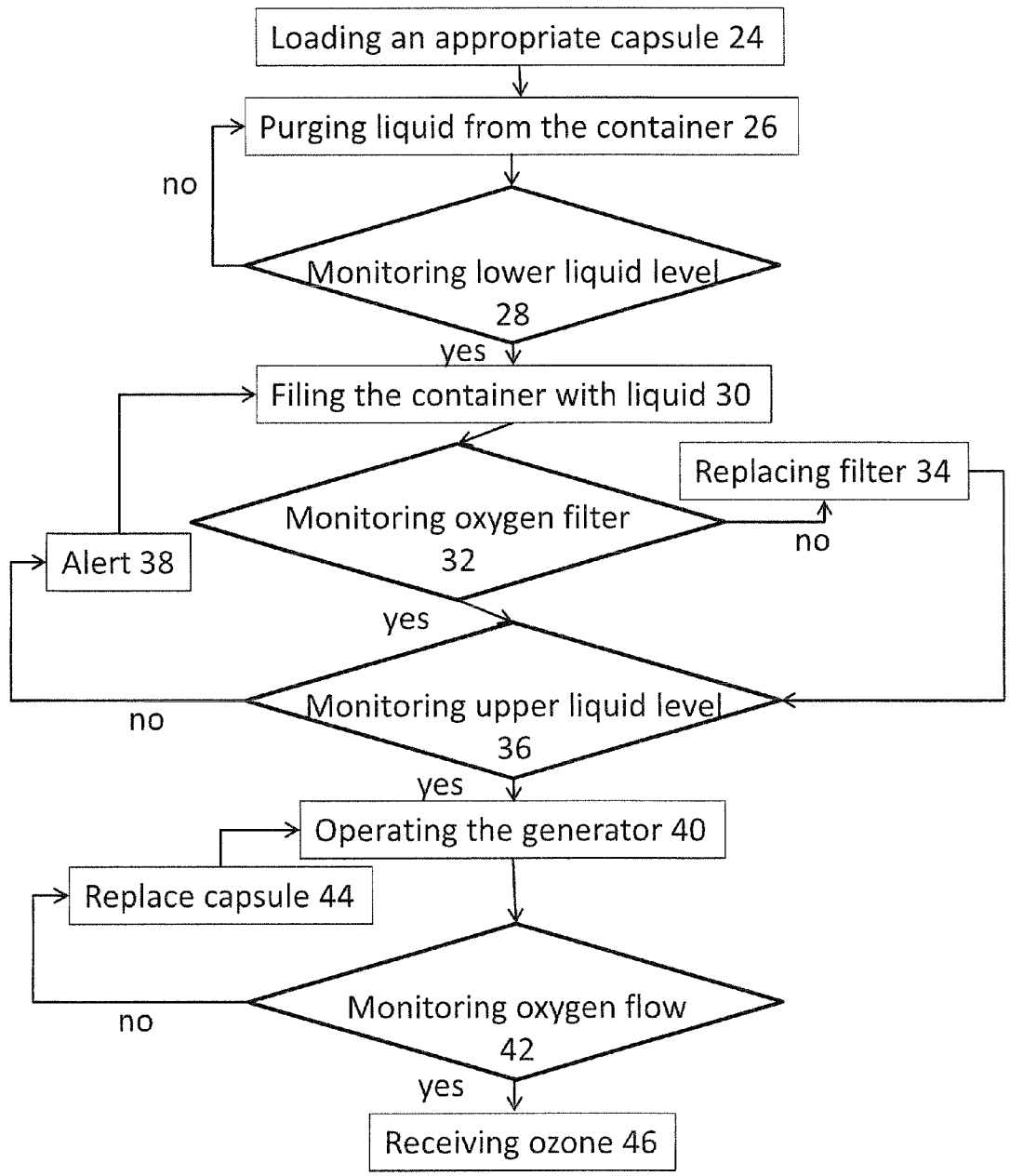
FIG. 7 illustrates flow-chart of a preferred embodiment of the method for on-site safe generation and delivering ozone at a specific amount.

Reference is now made to FIG. 7 illustrating a flow-chart of a preferred embodiment of the method for on-site safe generation and delivering ozone at a specific amount of the present invention, comprising: selecting an application-specific disposable capsule and loading it a receptacle mechanism of an ozone generator (24); the user then purges residual liquid from the container (26); and monitors minimal liquid level in the container (28) until the liquid in the container is indicated to be in the lowest level. This step is important to assure the liquid is fresh and lack in ozone. As long as the monitoring is negative, purging liquid is repeated; when the level reaches the lowest level, the user fills new liquid in the container (30); and then monitors the oxygen filter's saturation (32); and accordingly, the user replaces the oxygen filter (34) if the filter is indicated to be saturated; If the filter is in good performance or had been replaced, excess liquid level is monitored (36); and accordingly, the user is alerted (38) in case the level is not reached; after all security checks are positive, the user is initiating ozone generation (40); adequate oxygen flow is being monitored (42) to see whether oxygen is flowing. If there is no oxygen in the system, the capsule should be replaced (44). If all monitors are positive, ozone is generated and collected (46).

It should be mentioned that optionally, the system can generate ozone without passing it through water. The system is described herein after and accordingly, the method is adjusted.

Reference is now made to FIG. 8 illustrating a schematic operational view of yet another preferred embodiment (110) of the household appliance system for safe generation and delivering of ozone of the present invention, wherein a disposable capsule (300) encapsulating at least two separated components (not shown) of a chemical reaction based generation of a predetermined dose of oxygen, is placed through opening (87) in receptacle mechanism (800) and sealably connected to oxygen delivery tube (24*a*). Upon being sealably connected the separation between the chemical components encapsulated by the capsule is mechanically disrupted (not shown) and oxygen generated by the reaction flows through oxygen flow sensor (22) and subsequently through gas-wash oxygen filter (500) to be delivered by filtered-oxygen delivery tube (24*b*) to ozone generator (10), generating ozone for the duration of the application of voltage to the ozone generator, and delivering ozone by means of ozone delivery tube (24*c*).

In a preferred embodiment, the household appliance system for safe generation and delivering of ozone of the present invention, wherein application-specific doses of ozone are delivered by appropriately selecting at least one capsule configured to chemically generate a predetermined dose of oxygen, the system is comprising: a user interface for initiating the manipulating of the capsule and the disruption of the barrier therein; an ozone generator for generating ozone from the predetermined dose of oxygen, fluidically connected to the capsule; and, a computer processor capable of controlling at least generation of ozone by the ozone generator using data received from the user interface.

In a preferred embodiment, the household appliance system for safe generation and delivering of ozone of the present invention additionally comprises a flow sensor configured to regulate the cutting-off power to the ozone generator.

In a preferred embodiment, the household appliance system for safe generation and delivering of ozone of the present invention is further comprising a ozone impregnation system for receiving a liquid into which ozone from the ozone generator is dissolved and diffused by a liquid impregnator so as to produce ozone-rich liquid.

In a preferred embodiment, the household appliance system for safe generation and delivering of ozone of the present invention is further comprising a liquid-jet for dispensing ozone-rich liquid.

In a preferred embodiment, the household appliance system for safe generation and delivering of ozone of the present invention additionally comprises a filter for decomposing excess ozone and releasing benign oxygen into the environment.

In a preferred embodiment, the household appliance system for safe generation and delivering of ozone of the present invention additionally comprises at least one level sensor provided to at least one container so as to maintain a desirable level range of liquid.

In a preferred embodiment, the household appliance system for safe generation and delivering of ozone of the present invention, the at least one level sensor is mounted on the outer side of the container.

In a preferred embodiment, the household appliance system for safe generation and delivering of ozone of the present invention, is additionally comprising an ozone impregnation system, wherein the filling liquid is selected from a group including: water, oil, solution, or a combination thereof.

In a preferred embodiment, the household appliance system for safe generation and delivering of ozone of the present invention additionally comprises a filter between the disposable capsule and the ozone generator for ensuring pure and dry oxygen is delivered to the ozone generator.

In a preferred embodiment, the household appliance system for safe generation and delivering of ozone of the present invention, additionally comprises an ozone impregnation system, wherein the container is provided with a funnel through which filling of the container is administered.

In a preferred embodiment, the household appliance system for safe generation and delivering of ozone of the present invention, the ozone generator is selected from a group comprising: corona discharge electrode, cold plasma, UV light, vacuum UV light, or a combination thereof.

In a preferred embodiment of the household appliance system for safe generation and delivering of ozone, the system is of substantially moderate physical dimensions.

In a preferred embodiment, the household appliance system for safe generation and delivering of ozone of the present invention is configured with a sterile-electrode ozone generator such that the delivered ozone is medical-grade ozone.

In a preferred embodiment, the household appliance system for safe generation and delivering of ozone of the present invention is additionally comprising an ozone impregnation system, wherein the container is configured of ozone resistant material selected from a group consisting of glass, plastic, or a combination thereof.

In a preferred embodiment, the household appliance system for safe generation and delivering of ozone of the present invention is further comprising a see-through window through which the gas-wash oxygen filter is viewable, wherein the saturation of the filter can be monitored.

In a preferred embodiment, the household appliance system for safe generation and delivering of ozone of the present invention is further configured with visual indication for filter saturation.

In a preferred embodiment, the household appliance system for safe generation and delivering of ozone of the present invention further comprises at least one active damage prevention sensor for monitoring a state of potential damage either to the system or to the user, and acting to prevent it. For example, utilizing a sensor to sense an adequate level of liquid within a device and electronically preventing the user from operating the system until the sensor verifies that an adequate level of liquid is present.

In a preferred embodiment, the household appliance system for safe generation and delivering of ozone of the present invention, is configured with a defensive design that in addition to complying with health and safety regulations in a non-professional environment, also employs design to prevent the layperson user from misusing the device to an undesired or even harmful effect.

In a preferred embodiment, the household appliance system for safe generation and delivering of ozone of the present invention, is further configured with passive damage prevention design features that inherently contain or prevent damage to either the system or the user. For example the choice of materials, the physical strength of construction, excess pressure relieving valves, excess-ozone containment, excess-ozone decomposition, and directional control of excess by means of a 'pressure delta'.

In a preferred embodiment, the household appliance system for safe generation and delivering of ozone of the present invention, is configured as a module for the supply of ozone or ozone-rich liquid to an electrical appliance selected from a list including: a washing machine, fresh produce sanitizer, toothbrush, dishwasher, container sanitizer, fumigator, odor remover, vacuum cleaner, vaporizer, steamer, or a combination thereof.

In a preferred embodiment, the household appliance system for safe generation and delivering of ozone of the present invention is configured for outdoor usage.

In a preferred embodiment, the household appliance system for safe generation and delivering of ozone of the present invention is configured for professional medical use, wherein it meets medical grade standards.

In a preferred embodiment, the method for on-site safe generation and delivering ozone at a specific amount of the present invention additionally comprises purging the container from residual ozone-rich liquid, wherein the precise concentration of ozone in the liquid can be assured.

In a preferred embodiment, the method for on-site safe generation and delivering ozone at a specific amount of the present invention additionally comprises purging liquid from the container until receiving an alert from at least one liquid level range sensor.

In a preferred embodiment, the method for on-site safe generation and delivering ozone at a specific amount of the present invention additionally comprises monitoring a faulty capsule by means of an oxygen flow sensor and replacing a faulty capsule.

In a preferred embodiment, the method for on-site safe generation and delivering ozone at a specific amount of the present invention additionally comprises filling the container with a predetermined volume of liquid, wherein an application-specific concentration of ozone in the liquid is assured by the ratio between the application specific amount of ozone generated and the predetermined volume of liquid.

In a preferred embodiment of the disposable capsule of the present invention, a dose of oxygen is released from a capsule encapsulating at least two components of chemical reaction based generation of oxygen, wherein the components are precision measured to a achieve the predetermined dose.

In a preferred embodiment of the disposable capsule of the present invention, the capsule is provided with an opening seal configured to prevent moisture from entering the capsule during storage.

In a preferred embodiment of the disposable capsule of the present invention, the capsule is color coded or otherwise visibly marked in accordance with an application-specific amount of ozone to be generated.

In a preferred embodiment of the disposable capsule of the present invention, the capsule is provided with a safety pressure valve configured as a weak-point section of the capsule housing such that the weak-point ruptures in the event of pressure build-up within said capsule due to blockage of the opening of the capsule.

In a preferred embodiment of the disposable capsule of the present invention, the capsule is provided with a lance that is fluidically connected to one end of the capsule, wherein the one end is configured to conduct external manipulation of the capsule through the lance to the impermeable barrier.

The invention claimed is:

1. An appliance for delivering of an ozone-rich solution comprising:
   a capsule receptacle mechanism configured to (i) receive at least one capsule that comprises at least one chemical reactant that upon contact with water generates a dose of oxygen and to (ii) controllably disrupt the at least one capsule to permit said contact and generation of said dose of oxygen;
   the capsule receptacle mechanism being fluidically connected to an ozone generator to deliver the generated oxygen thereto;
   the ozone generator being configured to receive the dose of oxygen and generating ozone therefrom, the ozone generator being fluidically connected to an ozone impregnation system to deliver the generated ozone thereto;
   the ozone impregnation system comprising a liquid container to hold an aqueous liquid the ozone impregnation system configured to receive the generated ozone and impregnating the aqueous liquid in the liquid container to thereby generate an ozone-rich solution; and
   a delivery system fluidically connected to said impregnation system for delivering a jet of the ozone-rich solution.

2. The appliance as claimed in claim 1, wherein said ozone generator is configured to being activated for at least as long as oxygen is generated.

3. The appliance as claimed in claim 1, further comprising a user interface configured to activate said receptacle mechanism to thereby initiate oxygen generation.

4. The appliance as claimed in claim 1, further comprising a sensor configured to sense the flow of oxygen to thereby regulate power to the ozone generator.

5. The appliance as claimed in claim 1, wherein said ozone generator is selected from a group of ozone generators comprising: corona discharge electrode, cold plasma, UV light, vacuum UV light, or a combination thereof.

6. The appliance as claimed in claim 1, wherein volume of said liquid in said container is regulated to control the ozone concentration within said ozone-rich solution.

7. The appliance as claimed in claim 1, comprising a decomposing filter configured to decompose excess gaseous ozone into oxygen and release the oxygen to the environment.

8. The appliance as claimed in claim 7, wherein said ozone generator is a corona discharge ozone generator comprising a sterile electrode.

9. The appliance as claimed in claim 1, further comprising a filter configured to filter gas delivered from said capsule receptacle mechanism to said ozone generator.

10. A system for delivering of an ozone-rich solution, comprising:
    an appliance configured to deliver an ozone-rich solution that comprises:
    a capsule receptacle mechanism configured to (i) received at least one capsule that comprises at least one chemical reactant that upon contact with water generates a dose of oxygen and to (ii) controllably disrupt the at least one capsule to permit said contact and generate said dose of oxygen;

the capsule receptacle mechanism being fluidically connected to an ozone generator to deliver the generated oxygen thereto, the ozone generator being configured to receive the dose of oxygen and generate ozone therefrom, the ozone generator being fluidically connected to an ozone impregnation system to deliver the generated ozone thereto, the ozone impregnation system comprising a liquid container to hold an aqueous liquid, the ozone impregnation system configured to receive the generated ozone and impregnating the aqueous liquid in the liquid container to thereby generate an ozone-rich solution, and comprises a delivery system fluidically connected to said impregnation system for delivering a jet of the ozone-rich solution; and comprising at least one disposable capsule that comprises at least one chemical reactant that upon contact with water generates a dose of oxygen and that is configured to be received within said capsule receptacle mechanism.

11. The system as claimed in claim 10, wherein said at least one disposable capsule is configured to contain a sufficient amount of chemical reactant to generate at least one predetermined dose of oxygen.

12. The system as claimed in claim 10, wherein said at least one disposable capsule comprises at least two compartments.

13. A method for on-site safe generation and delivering a jet of an ozone-rich solution comprising:

reacting at least one reactant contained in a capsule with water to generate oxygen;

transferring the oxygen to an ozone generator to generate ozone therefrom;

contacting the ozone with water to thereby impregnate the water with the ozone and obtain an ozone-rich solution; and outputting a jet of said ozone-rich solution.

14. The method as claimed in claim 13, wherein the amount of the at least one reactant is selected to be sufficient to obtain a predetermined dose of oxygen and a consequent predetermined dose of ozone.

15. The method as claimed in claim 13, wherein said capsule comprises at least two compartments.

16. The method as claimed in claim 15, wherein one of the compartments contains said at least one reactant and the other compartment contains water.

17. The method as claimed in claim 13, further comprising decomposing excess ozone.

18. The method as claimed in claim 13, further comprising monitoring oxygen flow to thereby regulate operation of the ozone generator.

* * * * *